United States Patent
Bui et al.

(10) Patent No.: US 9,622,958 B2
(45) Date of Patent: Apr. 18, 2017

(54) COSMETIC COMPOSITION INCLUDING HYPERBRANCHED FUNCTIONAL POLYMER

(71) Applicant: L'OREAL, Paris (FR)

(72) Inventors: Hy Si Bui, Piscataway, NJ (US); Christopher Pang, New York, NY (US)

(73) Assignee: L'OREAL, Paris (FR)

( * ) Notice: Subject to any disclaimer, the term of this patent is extended or adjusted under 35 U.S.C. 154(b) by 15 days.

(21) Appl. No.: 14/218,229

(22) Filed: Mar. 18, 2014

(65) Prior Publication Data
US 2015/0265519 A1 Sep. 24, 2015

(51) Int. Cl.
| A61Q 1/10 | (2006.01) |
| A61K 8/81 | (2006.01) |
| A61K 8/31 | (2006.01) |

(52) U.S. Cl.
CPC .............. *A61K 8/8141* (2013.01); *A61K 8/31* (2013.01); *A61K 8/8147* (2013.01); *A61Q 1/10* (2013.01); *A61K 2800/49* (2013.01); *A61K 2800/544* (2013.01); *A61K 2800/594* (2013.01)

(58) Field of Classification Search
None
See application file for complete search history.

(56) References Cited

U.S. PATENT DOCUMENTS

| 4,104,262 | A | 8/1978 | Schade |
| 6,517,823 | B1 | 2/2003 | Norman et al. |
| 7,314,904 | B2 * | 1/2008 | Nadolsky .............. C08F 210/14 526/219.6 |
| 7,582,719 | B1 | 9/2009 | Tan et al. |
| 2005/0014664 | A1 | 1/2005 | Nadolsky et al. |
| 2010/0028284 | A1 | 2/2010 | Atis et al. |
| 2011/0094533 | A1 * | 4/2011 | Dempsey et al. ............ 132/216 |
| 2011/0177016 | A1 * | 7/2011 | Aliano ..................... A61K 8/31 424/70.7 |
| 2011/0280817 | A1 | 11/2011 | Ramadan et al. |
| 2013/0084255 | A1 | 4/2013 | Li et al. |
| 2013/0084256 | A1 | 4/2013 | Li et al. |
| 2013/0236406 | A1 | 9/2013 | Tong et al. |
| 2013/0236407 | A1 | 9/2013 | Tong et al. |
| 2013/0236408 | A1 | 9/2013 | Bui et al. |
| 2013/0236409 | A1 | 9/2013 | Bui et al. |

FOREIGN PATENT DOCUMENTS

| EP | 1367080 A1 | 12/2003 |
| WO | 2008155059 A2 | 12/2008 |

OTHER PUBLICATIONS

U.S. Appl. No. 14/218,263, filed Mar. 18, 2014, Bui et al.
P.A. Steward, J. Hearn, M.C. Wilkinson, An overview of polymer latex film formation and properties, Advances in Colloid and Interface Science 86 (2000) 195-267; www.elsevier.nl/locate/cis.
J.L. Keddie, Film formation of latex, Materials Science and Engineering, 21 101-170, Reports: A Review Journal, 1997 Elsevier Science S.A.
J.Y. Charmeau, E. Kientz, Y. Holl, Adhesion of latex films; influence of surfactants, Progress in Organic Coatings 27 (1996) 87-93, Elsevier Science S.A.
J.Y. Charmeau, R. Berthet, C. Gringreau and Y. Holl, E. Kientz, Effects of film structure on mechanical and adhesion properties of latex films, Int. J. Adhesion and Adhesives 7 (1997) 169-176 vol. 12, Elsevier Science Limited, printed in Great Britain.
D.I. Lee, The effects of latex coalescence and interfacial crosslinking on the mechanical properties of latex films, Polymer 46 (2005) 1287-1293, Science Direct, www.elsevier.com/locate/polymer.
A. Olah, M.A. Hempenius, S. Zou, G.J. Vancso, Adhesion studies of latex film surfaces on the meso- and nanoscale, Applied Surface Science 252 (2006) 3714-3728, www.elsevier.com/locate/apsusc.
S. Kiil, Drying of latex films and coatings: Reconsidering the fundamental mechanisms, Progress in Organic Coatings 57 (2006) 236-250, www.elsevier.com/locate/progcoat.
International Search Report and Written Opinion issued May 22, 2015 in PCT/IB2015/051984.

* cited by examiner

*Primary Examiner* — Jyothsna Venkat
(74) *Attorney, Agent, or Firm* — Oblon, McClelland, Maier & Neustadt, L.L.P.

(57) ABSTRACT

The present invention relates to a cosmetic composition comprising a latex film forming polymer, a hyperbranched functional polymer, an organic solvent and water. The compositions of the present invention may optionally contain at least one colorant. The invention also relates to a method for making up and/or enhancing the appearance of a keratinous substrate, in particular lashes, by applying these compositions to the keratinous substrate.

4 Claims, 7 Drawing Sheets

COSMETIC COMPOSITION INCLUDING HYPERBRANCHED FUNCTIONAL POLYMER

TECHNICAL FIELD

The present invention relates to a cosmetic composition and method for making up and/or enhancing the appearance of a keratinous substrate, comprising at least one latex film forming polymer, at least one hyperbranched functional polymer, at least one organic solvent and water. The compositions of the present invention may optionally contain at least one colorant.

BACKGROUND OF THE INVENTION

Makeup products, especially mascaras, are expected to have good wear and transfer resistance properties. With regard to this expectation, currently marketed mascaras are typically comprised of an emulsion of water and waxes to provide volume, length, and other attributes. Mascaras often also include one or more polymers to improve these properties. Illustrations of these polymers include silicone resins, polyacrylates and lattices. See, U.S. Pat. No. 6,517,823 and US2010/0028284. However, the above-mentioned polymers, which are advantageous in terms of wear and transfer-resistance properties, are often found by consumers to be difficult to spread and provide an undesirable tacky feeling. Moreover, the current long wear mascaras typically need to be reapplied approximately every 12-16 hour period. There remains a need to provide make up, particularly mascara, which affords longer wear (no flaking, stable color, does not transfer), for five (5) days or more (extremely long wear) and is still stable and comfortable to the consumer.

The inventors have found that the combination of a latex film forming polymer, a hyperbranched functional polymer a solvent, and water, in the stated amounts, and even in the absence of fats, provides a very stable and comfortable long wear cosmetic composition that enables the manufacture of an extreme wear mascara that last up to 5 days after application without flaking and with improved adhesion to the lashes ("extreme long wear").

While the use of hyperbranched functional polymers in cosmetics has previously been discussed (for example in US2013/0236407 (L'Oreal), 2013/0236408 (L'Oreal) and 2013/0236409 (L'Oreal), its ability to lower the glass transition temperature (Tg) latex film forming polymers thereby yielding a film with improved resistance to mechanical stress and improved adhesion to lashes is unexpected. These properties enable mascara the compositions of the invention to have extremely long wear.

BRIEF SUMMARY OF THE INVENTION

The present invention relates to homogeneous cosmetic compositions for making up and/or enhancing the appearance of keratinous substrates comprising:
  (a) at least one latex film forming polymer;
  (b) at least one hyperbranched functional polymer;
  (c) at least one organic solvent;
  (d) water; and
  (d) optionally, at least one pigment;
wherein said composition has a viscosity greater than or equal to 100 Pa·s and a pH of from about 6 to about 8.

According to another aspect of the present invention, there is provided a method of making up and/or enhancing the appearance of a keratinous substrate, in particular eye lashes, comprising applying onto the keratinous substrate the above-disclosed composition, wherein the composition provides a creamy, flexible film texture, great comfort and transfer resistance properties for up to 5 days of wear.

DESCRIPTION OF THE INVENTION

Other than in the operating examples, or where otherwise indicated, all numbers expressing quantities of ingredients and/or reaction conditions are to be understood as being modified in all instances by the term "about."

"About" as used herein means within 10% of the indicated number (e.g. "about 10%" means 9%-11% and "about 2%" means 1.8%-2.2%).

"At least one" means one or more and thus includes individual components as well as mixture/combinations.

The term "glass transition temperature" (Tg) generally refers to the temperature at which amorphous material changes from a glassy solid state to a rubbery state. The temperature may be measured by standard techniques in the art, such a Differential Scanning Calorimetry (DSM), e.g., according to a standard protocol such as ASTM D3418-97 standard.

"Keratinous substrate" may be chosen from, for example, hair, eyelashes, lip, and eyebrows, especially eye lashes.

"Low Tg" or "Low Glass Transition Temperature" as used herein to describe to the films made with the compositions of the invention means that the films have a glass transition temperature (Tg) of from about 0° C. to about 6° C.

"Polymers" as defined herein, include homopolymers and copolymers formed from at least two different types of monomers.

"Percent strain" (or sometimes referred to as percent elongation) as used herein is the amount of deformation (here elongation or stretch) that a film according to the invention experiences when stressed (e.g. pulled) compared to its original shape/size. For example, if a 10 cm film is deformed so that it becomes 11 cm long, the strain is (11-10)/10=0.1, which can also be expressed in percent measurement, in this example 10%.

"Water-dispersible" with respect to the film forming polymer herein means that the polymer is dispersible in water at 25° C. in an amount of at least 70% in the presence of a surfactant.

The "wear" of compositions as used herein, refers to the extent by which the composition remains creamy and flexible when applied, for example to lashes, does not substantially flake and retains the same or substantially the same color as at the time of application, as viewed by the naked eye, after a certain period or an extended period of time. Wear properties may be evaluated by any method known in the art for evaluating such properties. For example, wear may be evaluated by a test involving the application of a composition to eye lashes and evaluating the color of the composition after a specified period of time. Further, these characteristics may be evaluated with respect to other compositions, such as commercially available compositions.

"Extreme wear" with respect to mascara refers to mascara having good wear properties for up to at least 5 days after application.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

The invention relates to a cosmetic composition comprising
(a) at least one latex film forming polymer;
(b) at least one hyperbranched functional polymer;
(c) at least one organic solvent;
(d) water; and
(e) optionally, at least one pigment;
wherein said composition has a viscosity greater than or equal to 100 Pa·s, at 0.1/s shear rate, and a pH of from about 6 to about 8.

In another embodiment the invention relates to a cosmetic composition comprising
(a) at least one latex film forming polymer having a glass transition temperature from about −15° C. to about 90° C.;
(b) at least one hyperbranched polyacid;
(c) at least one organic solvent;
(d) water; and
(e) optionally, at least one pigment;
wherein said composition has a viscosity greater than or equal to 100 Pa·s, at 0.1/s shear rate, and a pH of from about 6 to about 8.

Another embodiment of the invention relates to a cosmetic composition comprising
(a) from about 25% to about 37.5%, by weight, of at least one latex film forming polymer selected from acrylate copolymers and derivatives thereof having a glass transition temperature from about −15° C. to about 90° C.;
(b) from about 0.5% to about 10%, by weight, of at least one hyperbranched polymer selected from a polyacid;
(c) from about 3.5% to about 15%, by weight, of at least one organic solvent;
(d) from about 10% to about 60%, by weight, water; and
(e) optionally, at least one pigment;
wherein said composition has a viscosity from about 300 Pa·s to about 1000 Pa·s, at 0.1/s shear rate, and a pH of from about 6 to about 8, and wherein all weights are relative to the total weight of the composition.

In a preferred embodiment, the compositions of the invention result in a film having a percent strain at break point of up to about 1000%, typically at least from about 50% to about 500%, most typically at least from about 100% to 300% strain, at room temperature and dry conditions (11% humidity). This reflects the ability of the films to stretch up to 1000% without breaking thereby yielding a mascara composition that is flexible and does not flake. Strain measurements were made on films that were made by pouring the composition of the invention into a Teflon-coated petri dish, coating the bottom of the petri dish with the film, permitting the film to dry, peeling the film from the petri dish and subjecting it to deformation testing. Percent strain is measured as $(L-L_0)/L_0 \times 100 = \%$ strain, wherein L is maximum length of film stretch prior to breaking and $L_0$ is the length of the un-stretched film.

It was unexpectedly found that incorporating the hyperbranched functional polymer into the anionic styrene acrylate copolymer helped plasticize the composition by lowering the Tg of the styrene acrylate copolymer yielding films having a glass transition temperature (Tg) optimally between 0° C. and 5° C. This overall lowering of Tg makes the resulting films softer and more flexible thereby less likely to break. The percent strain was also increased from 4% to 300% while maintaining a high break stress. This changed the original film property from being brittle to being ductile. This softer and more flexible texture is especially desirable with mascaras as it reduces the flaking of the product. The formulas of the invention thus unexpectedly increased the wear of a mascara composition from 2 days to up to about 5 days.

In a particular embodiment, the compositions of the invention result in a film having a Tg of from about 0° C. to about 6° C., optimally from about 0° C. to about 5° C., as measured by differential scanning calorimetry (DSC).

In an embodiment, the viscosity of the inventive compositions, measured with an AR G2 Rheometer, is greater than or equal to 100 Pa·s, preferably from about 300 Pas to about 1000 Pa·s, at 0.1/s shear rate, and a viscosity greater than or equal to 0.5 Pa s, preferably from 0.5 Pa s to 1.6 Pa·s at 1000/s shear rate, including all ranges and ranges therebetween. The viscosity is generally measured over a 10 minute interval.

In another embodiment, the pH of the compositions of the invention at 25° C. ranges from about 6 to about 8, most preferably about 7.5+/−0.3.

Latex Film Forming Polymer (a)

The at least one latex film forming polymer may be chosen from random styrene acrylate copolymers and derivatives thereof. Such copolymers are described, for example, in US 2013/0084256 and US 2010/0028284, both of which are herein incorporated by reference. In an embodiment the at least one styrene acrylate copolymer and derivatives thereof may be chosen from those copolymers that are water-dispersible and have a glass transition temperature (Tg) ranging from about −15° C. to about 90° C., such as from about 0° C. to about 50° C. The term "water-dispersible" with respect to polymers is well-understood by one skilled in the art. See, e.g. U.S. Pat. No. 4,104,262. By way of non-limiting example, the at least one film-forming styrene acrylate copolymer may be chosen from styrene/acrylates/ammonium methacrylate copolymers, styrene/acrylates copolymers emulsion (INCI name), styrene acrylic copolymers, and mixtures thereof. Exemplary commercial random styrene acrylate copolymer products that may be used in the invention include, but are not limited to, SYNTRANT™ 5760 (styrene/acrylates/ammonium methacrylate copolymer (and) butylene glycol (and) sodium laureth-12 sulphate (INCI name), commercially available from Interpolymer Corporation); JONCRYL™ 77 (styrene/acrylates copolymer in the form of an ammonia salt, along with water and polypropylene glycol, available from BASF Performance Chemicals); and RHOPLEX™ P376 (styrene/acrylates copolymer available from Dow Chemical Company).

In a particular embodiment the film forming the latex film former is styrene/acrylate copolymer.

The at least one film forming styrene acrylate copolymer may be present in the cosmetic composition in an amount ranging from about 25% to about 37.5% by weight, such as from about 30% to about 36.5% by weight, most particularly from about 34% to about 36% by weight, including all ranges and subranges therebetween, relative to the total weight of the composition.

Hyperbranched Functional Polymer (b)

Hyperbranched Polymers

Generally, hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have any of the following: an extremely branched structure around a core; successive generations or layers of branching; layer of end chains.

The growth of the polymer is made possible by repeating units of single monomers or linear chains added onto the central core. The end unit of the single monomer or linear chain can be functionalized to provide junction points (i.e., linkage points) for further growth of the polymer. The final form of the hyperbranched polymer exhibits a tree-like structure without any symmetry or regularity.

The synthesis of hyperbranched polymer can be produced by single monomer methodology (SMM) or double monomer methodology (DMM) (Gao and Yan, 2004). For SMM, polymerization involves an ABx, AB* or a latent ABx monomer through generally four different types of reaction mechanism: polycondensation of ABx monomers, self-condensing vinyl polymerization (SCVP), self-condensation ring opening polymerization (SCROP) and proton transfer polymerization (PTP). For DMM, a direct polymerization is possible with two types of monomers or monomer pairs, the most notable being the polymerization of "A2+Bn, n≥2", and the couple-monomer methodology (CMM) has also been used.

There are several ways to characterize the topology of a hyperbranched polymer, such as, by its degree of branching and the Wiener index. The degree of branching is defined as $B=2D/(2D+L)$ where D is the number of fully branched units and L is the number of partially reacted units (Holter et al., 1997). For a completely linear polymer, $B=0$ and for a fully branched hyperbranched polymer $B=1$. The Wiener index states the sum of paths or branches between all pairs of non-hydrogen atoms in a molecule (Wiener, 1947). It is defined as $$W = \frac{1}{2}\sum_{j=1}^{N_s}\sum_{i=1}^{N_s}d_{ij}$$

where Ns is the degree of polymerization and dij is the number of bonds separating site i and j of the molecule. For two polymers with equal number of molecular weight, the linear polymer will have a smaller Wiener number than the hyperbranched polymer.

The end groups of a hyperbranched polymer can be reacted with other chemical entities to obtain a particular functionality on the ends of chains.

Hyperbranched Functional Polymers

"Hyperbranched functional polymers" refers to polymers comprising at least two, for example three, polymeric branches, forming either the main branch or a secondary branch, and each comprising at least one trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point (i.e., linkage point) between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least one trifunctional branch" means the junction points (i.e., linkage points) between at least three polymeric branches, for example n polymeric branches (wherein n=3 or more), of which n−1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

In a preferred embodiment the at least one hyperbranched functional polymer is selected from at least one hyperbranched polyacid.

Hyperbranched Polyacid

In a preferred embodiment, the compositions of the invention comprise at least one hyperbranched polyacid. Hyperbranched polyacid refers to the fact the functional groups of the hyperbranched functional polymer are substituted with carboxylic acid groups.

The at least one hyperbranched polyacid compound of the present invention has at least two carboxyl groups. Preferably, the hyperbranched polyacid has a carboxyl number of at least 3, more preferably of at least 10, more preferably of at least 50, and more preferably of at least about 150. According to preferred embodiments, the at least one hyperbranched polyacid has a carboxyl number between 50 and 250, preferably between 75 and 225, preferably between 100 and 200, preferably between 125 and 175, including all ranges and subranges there between such as 90 to 150.

Suitable examples of hyperbranched polyacids can be found in U.S. Pat. No. 7,582,719 and US2013/0236409, the entire contents of which are hereby incorporated by reference.

Unsaturated functionalizing compounds useful with the present invention include, but are not limited to, carboxylic acids, carboxylic acid esters, amides, ethers, amines, phosphate esters, silanes and alcohols. Examples of such carboxylic acids include, but are not limited to, 5-hexenoic acid, 6-heptenoic acid, 10-undecylenic acid, 9-decenoic acid, oleic acid, and erucic acid. Also useful are esters of these acids with linear or branched-chain alcohols having from about 1 to about 10 carbon atoms, as well as triglycerides containing olefinic unsaturation in the fatty acid portion such as tall oil, fish oils, soybean oil, linseed oil, cottonseed oil and partially hydrogenated products of such oils. Other useful materials include olefinic alcohols such as allyl alcohol, 9-decen-1-ol, 10-undecylenyl alcohol, oleyl alcohol, erucyl alcohol, acetic acid or formic acid esters of these alcohols, C1-C4 alkyl ether derivatives of these alcohols and formamides or acetamides of unsaturated amines such as oleylamine, erucylamine, 10-undecylenylamine and allylamine.

According to preferred embodiments, the at least one hyperbranched acid compound has a molecular weight (Mw) between about 500 g/mol and about 100,000 g/mol, typically between about 800 g/mol and about 50,000 g/mol, preferably between about 1000 g/mol and about 8,000 g/mol, most preferably about 5,000 g/mol, including all ranges and subranges therebetween.

According to preferred embodiments, the at least one hyperbranched polyacid compound has a viscosity at 210° F. of between 0.01 Pa·s and 10 Pa·s, such as between 0.1 and 7 Pa·s, and such as between 0.3 and 2 Pa·s, more particularly about 0.45 Pa·s, including all ranges and subranges therebetween. The viscosity is determined using Brookfield viscometer at 210° F. by ASTMD-3236MOD method.

According to preferred embodiments, the at least one hyperbranched acid compound has an acid number between about 20 and about 400 mg/KOH, more preferably between about 30 and about 300 mg/KOH, and even more preferably between about 50 and about 100 mg/KOH, in particular about 80 mg/KOH.

In an embodiment the hyperbranched polyacid is a semi-crystalline polymer having a glass transition temperature (Tg) of from about −30° C. to about 0° C., particularly from about −20° C. to about −1° C., more typically from about −15° C. to about −5° C., and a melting point of from about 45° C. to about 100° C., typically from about 50° C. to about 90° C., most typically from about 55° C. to about 85° C.

A particularly preferred acid functional olefinic polymer is C30+olefin/undecylenic acid copolymer available from New Phase Technologies under trade name Performa V™-6112.

The at least one hyperbranched polyacid compound may be present in the composition of the invention in an amount ranging from about 0.5% to about 10% by weight, more particularly from about 1% to about 6% by weight, most particularly from about 2% to about 3% by weight, including all ranges and subranges therebetween, relative to the total weight of the composition.

Organic Solvent (c)

The composition of the invention also comprises a cosmetically acceptable solvent typically selected from a cosmetically acceptable organic solvent. Preferred organic solvents are non-aromatic oils such as, for example, non-aromatic hydrocarbon-based oils and non-aromatic silicone oils. In one embodiment, the non-aromatic oil is a volatile oil.

As used herein, the term "volatile oil" means an oil that is capable of evaporating on contact with keratin materials in less than one hour, at approximately room temperature and atmospheric pressure (760 mmHg). Volatile oils that may be used according to the disclosure include, but are not limited to, volatile cosmetic oils, which are liquid at room temperature and have a non-zero vapor pressure at room temperature and atmospheric pressure, said vapor pressure ranging, for example, from about 0.13 Pa to about 40,000 Pa (10-3 to 300 mmHg), such as from about 1.3 Pa to about 13,000 Pa (0.01 to 100 mmHg), or from about 1.3 Pa to about 1,300 Pa (0.01 to 10 mmHg). In contrast, non-volatile oils have a vapor pressure of less than about 1.33 Pa (0.01 mmHg).

According to various embodiments, the non-aromatic hydrocarbon-based oils may be chosen from:
- hydrocarbon-based oils comprising from 8 to 16 carbon atoms, for example, C8-C16 branched alkanes such as C8-C16 isoalkanes of petroleum origin (also known as isoparaffins), for instance isododecane (also known as 2,2,4,4,6-pentamethylheptane), isodecane, and isohexadecane, and, for example, the oils sold under the trade names Isopar® and Permethyl®; linear alkanes, for instance, n-dodecane (C12) and n-tetradecane (C14) sold by Sasol under the respective references Parafol 12-97 and Parafol 14-97, and mixtures thereof; the undecane-tridecane mixture, and mixtures of n-undecane (C11) and of n-tridecane (C13) obtained in Examples 1 and 2 of International Patent Application Publication No. WO 2008/155 059 assigned to the company Cognis, and mixtures thereof;
- linear and branched hydrocarbons of mineral or synthetic origin, such as petroleum jelly, polydecenes, hydrogenated polyisobutene such as Parleam®, squalane, liquid paraffins, and mixtures thereof;
- synthetic esters such as oils of formula R'1COOR'2 in which R'1 is chosen from linear and branched fatty acid residues comprising from 1 to 40 carbon atoms and R'2 is chosen from branched hydrocarbon-based chains comprising from 1 to 40 carbon atoms, with the proviso that R'1+R'2≥10, for instance purcellin oil (cetostearyl octanoate), isopropyl myristate, isopropyl palmitate, octyl palmitate, C12 to C15 alkyl benzoate, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl and polyalkyl heptanoates, octanoates, decanoates, and ricinoleates such as propylene glycol dioctanoate; hydroxylated esters such as isostearyl lactate, diisostearyl malate, and 2-octyldodecyl lactate; polyol esters and pentaerythritol esters;
- fatty alcohols that are liquid at room temperature, comprising a branched and/or unsaturated carbon-based chain comprising from 12 to 26 carbon atoms, for instance, octyldodecanol, isostearyl alcohol, oleyl alcohol, 2-hexyldecanol, 2-butyloctanol, and 2-undecylpentadecanol;
- higher fatty acids such as oleic acid, linoleic acid, linolenic acid, and mixtures thereof;
- hydrocarbon-based oils of plant origin such as triglycerides comprising fatty acid esters of glycerol, the fatty acids of which may have chain lengths comprising from 4 to 24 carbon atoms, these chains possibly being linear or branched, and saturated or unsaturated; for example, heptanoic and octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, and musk rose oil; shea butter; and caprylic/capric acid triglycerides, for instance those sold by the company Stéarineries Dubois or those sold under the names Miglyol 810®, 812® and 818® by the company Dynamit Nobel; and
- mineral oil.

According to one exemplary embodiment, the at least one non-aromatic oil is chosen from hydrocarbon-based oils comprising from 8 to 16 carbon atoms. For example, in at least one embodiment, the non-aromatic oil is selected from isodecane, isododecane, isohexadecane, and mixtures thereof.

The organic solvent may be present in the composition of the present invention in an amount ranging from about 4% to about 15% by weight, more preferably from about 5% to about 12% by weight, most preferably from about 6% to about 8% by weight, including all ranges and subranges therebetween, relative to the total weight of the composition.

Water (d)

The compositions for the invention also comprise water in an amount ranging from about 10% to about 60% by weight, preferably from about 20% to about 55% by weight, most typically from about 30% about 50% by weight, in particular about 35% by weight, including all ranges and subranges therebetween, relative to the total weight of the compositions.

Pigment(s)(e)

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention, including but not limited to, surface treatments with compounds such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. In an embodiment of the invention the pigment is present in an amount of from about 10% to about 15% by weight, more particularly 12% by weigh based on the total weight of the composition.

Additional Optional Additive(s)

A composition according to the invention may also comprise at least one agent usually used in cosmetics, chosen, for example, from: reducing agents; thickeners; film-forming agents that are especially hydrophobic, or are softeners, antifoams, moisturizers, or UV-screening agents; ceramides; cosmetic active agents; peptizers; fragrances; proteins; vitamins; propellants; hydrophilic or lipophilic, film-forming or non-film-forming polymers; lipophilic or hydrophilic gelling agents; and preservatives. Non-limiting examples of preservatives include phenoxyethanol and caprylyl glycol. A non-exhaustive listing of such ingredients is found in U.S. Pat. No. 7,879,316, the entire content of which is hereby incorporated by reference. Additional examples of additives may be found in the *International Cosmetic Ingredient Dictionary and Handbook* ($9^{th}$ ed. 2002, and subsequent editions).

In an embodiment, the composition includes at least one preservative selected from Phenoxyethanol, caprylyl glycol, and a mixture thereof.

If present, the above additives are typically found in an amount for each of them of between about 0.01% and about 10% by weight, most typically from about 0.5% to about 2% by weight, including all ranges and subranges therebetween, by weight relative to the total weight of the composition. A person skilled in the art will take care to select the constituents of the composition such that the advantageous properties associated with the invention are not, or are not substantially, adversely affected.

Cosmetic Methods

In an embodiment according to the invention, the compositions comprising a film forming latex polymer, a hyperbranched functional polymer, and a solvent can impart thickening and volumizing properties to the lashes and remain on the lashes in substantially the same form and amount for at least 5 days. Accordingly, another embodiment of the invention provides a method of making up/or enhancing the appearance of eyelashes by applying to the lashes topically the composition of the present invention in a sufficient amount to make up the lashes. The compositions may be applied to the eyelashes as needed, but preferably the composition does not need to be reapplied bot about 5 days.

Another embodiment of the invention relates to a method of improving long wear and adhesion of a mascara while retaining comfort, buildability, color intensity properties of said mascara by incorporating therein at least one forming latex polymer, at least one hyperbranched functional polymer, an organic solvent and water as described herein.

EXAMPLES

The following Examples are intended to be non-restrictive and explanatory only, with the scope of the invention being defined by the claims.

As used in herein INCI US stands for International Nomenclature of Cosmetic Ingredients US.

TABLE 1

Mascara Compositions

| INCI US | Control Composition X | Ex 1 | Ex 2 |
|---|---|---|---|
| styrene/acrylates copolymer (Joncryl ™ 77)(a) | 34.44 | 34.44 | 34.44 |
| C30 + olefin/undecylenic acid copolymer (Performa ™ VTM-6112)(b) | | 3 | 5 |
| isododecane (c) | | | 3.75 |
| iIsohexadecane (c) | 10 | 7 | 1.25 |
| water (d) | 34.94 | 34.94 | 34.94 |
| caprylyl glycol (preservative) | 1.1 | 1.1 | 1.1 |
| phenoxyethanol (preservative) | 0.7 | 0.7 | 0.7 |
| iron oxides | 12 | 12 | 12 |

All numerical values in the above Table are weight percent active.

Procedures

Method of Preparation of Mascaras

Hyperbranched polymer (polyacid) was first heated to 80° C. and predispersed in the oil phase. All the materials were then combined into container and placed in a speed mixer and mixed at 2750 rpm for 5 mins or until homogeneous. The mixture was then cooled to room temperature while mixing with a propeller blade before pouring to suitable size containers for future testing.

Figure 1A:
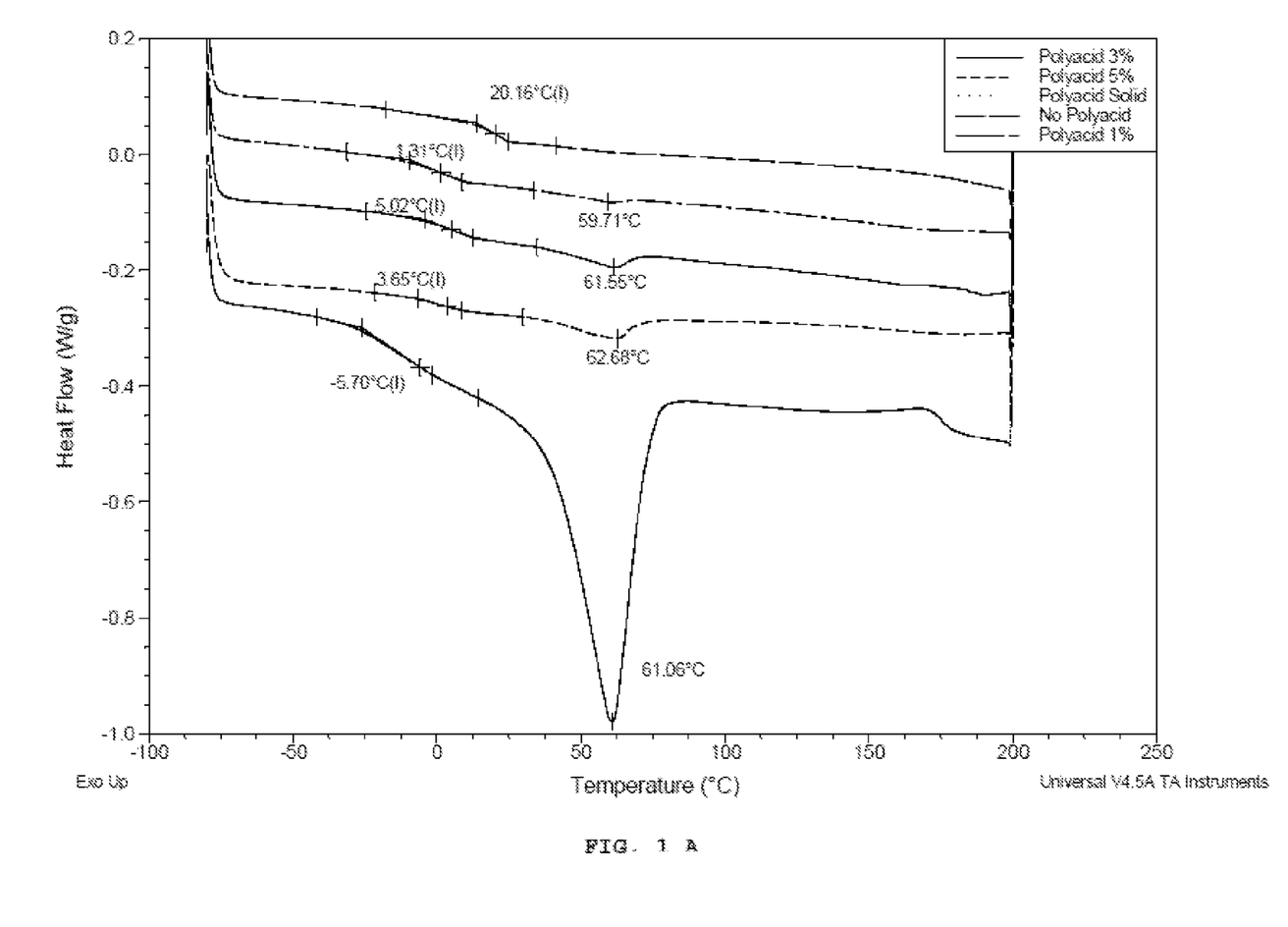
FIG. 1A and FIG. 1B are differential scanning calorimetric (DSC) scans showing that the incorporation of a polyacid in homogeneous polyacid/styrene acrylates copolymer film former composition can lower the Tg of the resulting films.
Figure 1B:
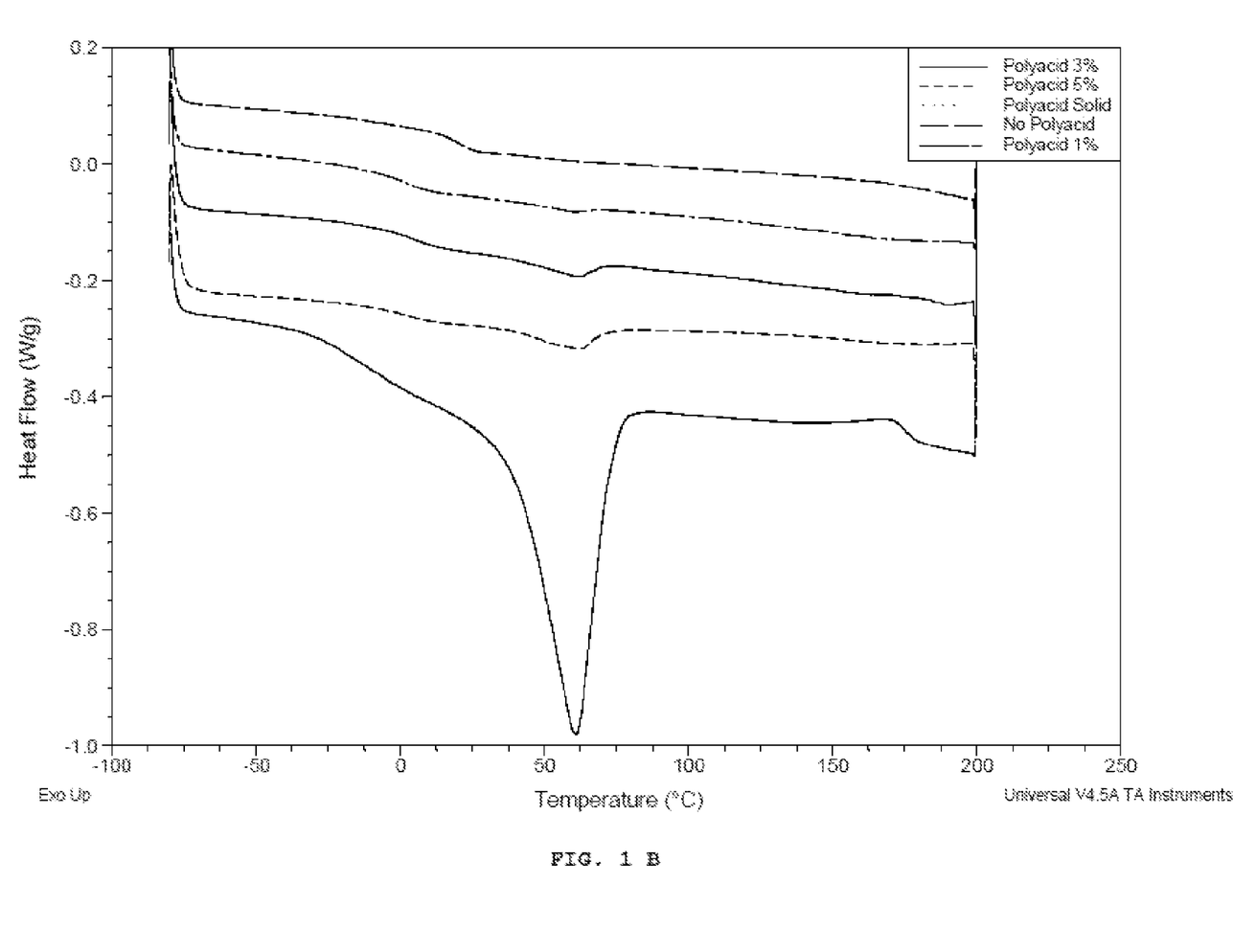

Assessment of Incorporation of Hyperbranched Polymer (Polyacid) on Tg of Resulting Film Mascara formulas incorporating the inventive compositions were drawn down on a glass plate using a draw dawn bar until the thickness of the resulting film was about 6 mil. The films were allowed to dry from overnight to a week. The dried films were then peeled from the plate and each was then subjected to DSC scanning to measure film softening. The results of this test are reported in Table 2 and FIG. 1.

TABLE 2

Tg and Melting Peak (MP) of Films

| Films with | Tg | Melting Peak of Film |
| --- | --- | --- |
| Latex, No Polyacid | 20.16° C. | 0 |
| Latex + 1% Polyacid | 1.31° C. | 59.71° C. |
| Latex + 3% Polyacid | 5.02° C. | 61.55° C. |
| Latex + 5% Polyacid | 3.65° C. | 62.68° C. |
| 100% Polyacid, no latex | −5.70° C. | 61.06° C. |

As is shown in Table 2 above and FIG. 1 infra, the scan of the film with polymer alone (no polyacid, top line) does not show softening (there is no dip in the line) in the tested temperature range. This means the film remains rigid (and breakable). In contrast, as increasing amounts of polyacid are added, the resulting films show softening in the tested temperature range. This means that even at low concentrations, the inclusion of hyperbranched polyacid in the compositions of the invention lowers the temperature at which the films exhibit softening behavior (the dip in the line) meaning the films are more flexible and less likely to break. In mascara formulations, this added film flexibility translates to less flaking. This was also confirmed in the in vivo tests discussed below.

In-Vivo Testing: Consumer Flash

The flake, smudge and overall wear properties of mascaras made with the inventive compositions, two commercially available comparator mascaras (A and B), and another comparative composition (C) were evaluated on test subjects. Each mascara was evaluated on 12-14 test subjects.

Protocol

Mascara was applied by the test subjects and worn for five (5) days without reapplication. The subjects otherwise maintained their normal routines, such as showering, etc.

Figure 2:
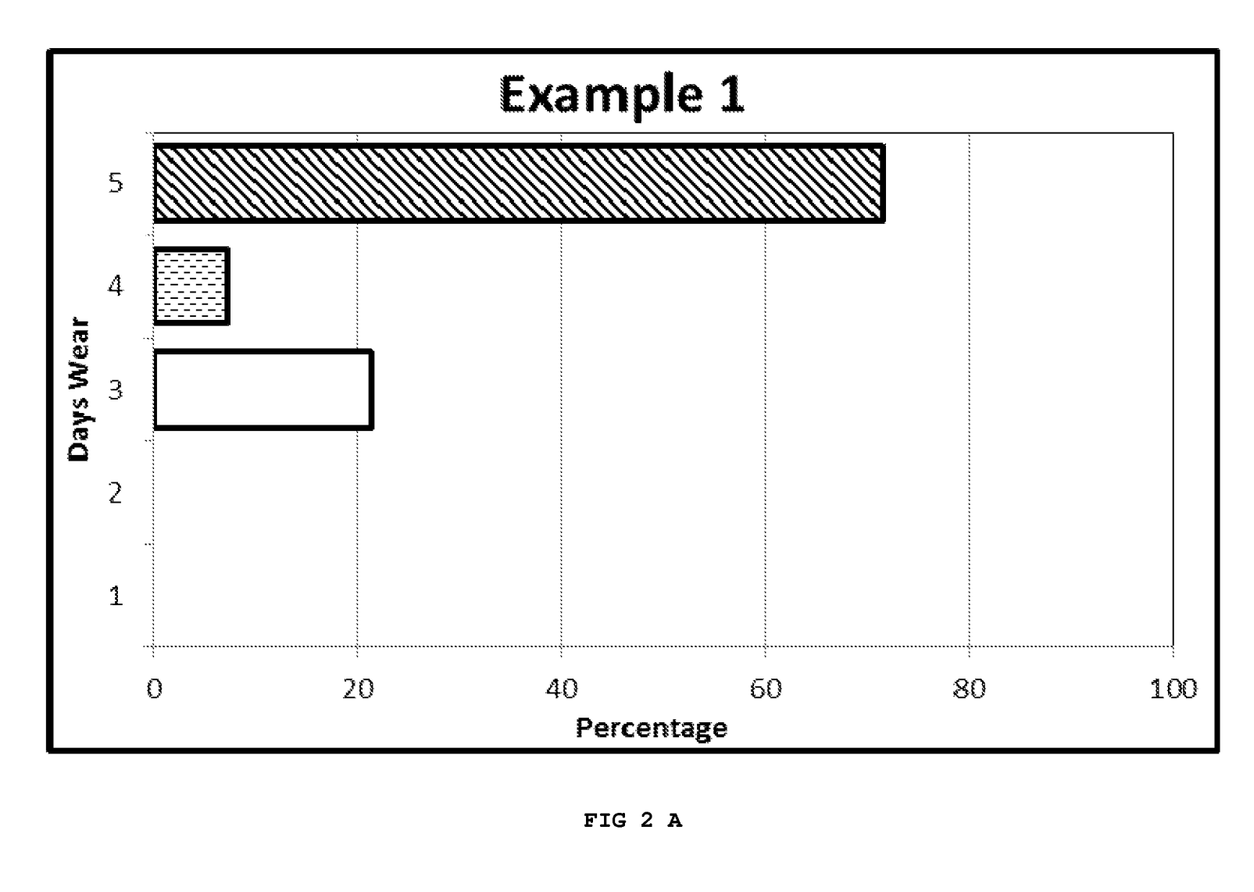
FIG. 2A-FIG. 2E are bar graphs containing results of a consumer wear test.

The results of the Consumer Flash test are provided below in Table 3 as well as in FIG. 2.

TABLE 3

Consumer Flash Test

| Example/ Comparator | Flake/smudge | Perception of 5-day Wear | Average Wear (days) | Ingredients |
| --- | --- | --- | --- | --- |
| Comparator A | 0 smudge Flaking at 2.8 days | 50% | 4.3 | MQ Resin |
| Ex. 2 | 0 smudge Flaking at 2.3 days | 67% | 4.6 | 5% polyacid |
| Ex. 1 | 0 smudge Flaking at 3.25 days | 71% | 4.5 | 3% polyacid |
| Comparator B (long wear mascara) | Smudging at 2 days; Flaking at 2.7 days | 27% | 3.9 | MQ resin + Rosinate |
| Comparator C | Smudging at 2 days; lasted 3 days; 0 flaking | 42% | 3.9 | MQ resin |

The results above (and tabulated in FIG. 2) show that including a polyacid in a styrene/acrylate copolymer-based mascara increases the durability and flexibility of the mascara thereby allowing it to stay on the lashes for up to about 5 days. With the inventive compositions, flaking was observed no earlier than about 3.25 days, which is substantially longer than commercially available, acrylate-based anhydrous long wear mascaras (Comparators B and C, standard technologies for "long wear" mascara). Moreover, the wear showed better, more product stayed on the lashes, and there was less smudging in comparison to the other mascaras tested.

It is to be understood that the foregoing describes preferred embodiments of the invention and that modifications may be made therein without departing from the spirit or scope of the invention as set forth in the claims.

The invention claimed is:

1. A mascara composition comprising:
   (a) from about 34 % to about 36 %, by weight, of a styrene/acrylate in the form of a latex film forming polymer having a glass transition temperature from about -15° C. to about 90° C.;
   (b) from about 2% to about 3%, by weight, of C30+olefin/ undecylenic acid copolymer
   (c) from about 6% to about 8%, by weight, of at least one organic solvent selected from the group consisting of isodecane, isododecane and isohexadecane;
   (d) from about 30% to about 50%, by weight, water; and
   (e) pigment.

2. The mascara composition of claim 1, which when applied to a surface and dried forms a film having a glass transition temperature of from about 0° C. to about 5° C.

3. A film formed by applying the mascara composition of claim 1 a surface, said film having a percent strain at breakpoint of from about 50% to about 500%.

4. A method of improving long-wear in a mascara composition comprising applying to the eyelashes a mascara composition according to claim 1.

* * * * *

UNITED STATES PATENT AND TRADEMARK OFFICE
CERTIFICATE OF CORRECTION

PATENT NO. : 9,622,958 B2  
APPLICATION NO. : 14/218229  
DATED : April 18, 2017  
INVENTOR(S) : Bui et al.

Page 1 of 1

It is certified that error appears in the above-identified patent and that said Letters Patent is hereby corrected as shown below:

In the Claims

Column 12, Line 54, "claim 1 a surface," should read --claim 1 to a surface,--.

Signed and Sealed this
Tenth Day of July, 2018

Andrei Iancu
*Director of the United States Patent and Trademark Office*